US005711304A

United States Patent [19]
Dower

[11] Patent Number: 5,711,304
[45] Date of Patent: Jan. 27, 1998

[54] SIGNAL PROCESSING APPARATUS AND METHOD FOR ADDING ADDITIONAL CHEST LEADS TO THE 12-LEAD ELECTROCARDIOGRAM WITHOUT ADDITIONAL ELECTRODES

[76] Inventor: Gordon Ewbank Dower, 1505 Tolmie St., Vancouver, Canada, V6R 4B5

[21] Appl. No.: 688,212

[22] Filed: Jul. 29, 1996

Related U.S. Application Data

[63] Continuation of Ser. No. 385,817, Feb. 9, 1995.
[51] Int. Cl.$^6$ ................................................. A61B 5/0402
[52] U.S. Cl. .................... 128/696; 128/699; 128/709; 128/710
[58] Field of Search ............................... 128/643, 644, 128/696, 697, 699, 700, 709, 710, 639, 902; 364/413.06

[56] References Cited

U.S. PATENT DOCUMENTS

| | | |
|---|---|---|
| 3,709,212 | 1/1973 | Koeblitz . |
| 3,757,778 | 9/1973 | Graham . |
| 3,884,221 | 5/1975 | Eastman . |
| 4,683,441 | 7/1987 | Naylor . |
| 4,742,831 | 5/1988 | Silvian . |
| 4,850,370 | 7/1989 | Dower . |
| 5,058,598 | 10/1991 | Nicklas et al. . |
| 5,217,020 | 6/1993 | Saltztein et al. . |
| 5,231,990 | 8/1993 | Gauglitz . |
| 5,339,823 | 8/1994 | Reinhold, Jr. . |
| 5,377,687 | 1/1995 | Evan et al. . |

FOREIGN PATENT DOCUMENTS

| | | |
|---|---|---|
| 2 272 770 | 5/1994 | United Kingdom . |

OTHER PUBLICATIONS

Instrumentation and Measurement Technology Conference, Washington, Apr. 25–27, 1989, No. 1989, 25 Apr. 1989, Institute of Electrical and Electronics Engineers, pp. 184–189, XP000041359 Perkusich a Et Al: "An Expert ECG Acquisition and Analysis System".

Medical and Biological Engineering and Computing vol. 25, No. 2, Mar. 1987, Stevenage GB, pp. 155–164, "Orthogonal Electrocardiogram derived from the limb and chest electrodes of the conventional 12–lead system".

Proceedings of Computers in Cardiology, IEEE Press New York US, 25–28 Sep. 1988, Washington D.C., U.S., pp. 449–451, XP002004856 J.A. Scherer Et Al: "Synthesis of the 12 Lead Electrocardiogram from a 3 Lead Semi–Orthogonal Subset using Patient-specific Linear Transfrmation Arrays".

*Primary Examiner*—Marvin M. Lateef
*Assistant Examiner*—Shawna J. Shaw
*Attorney, Agent, or Firm*—Shlesinger Arkwright & Garvey LLP

[57] ABSTRACT

Signal processing apparatus for use with an electrocardiograph monitoring activity of the human heart is disclosed. The apparatus receives input signals from electrodes attached to the body of a subject whose heart activity is being monitored. These electrodes include chest electrodes positioned at conventional positions V1, V2, V3, V4, V5 and V6 of the body and limb electrodes positioned at conventional positions RA, LA and LL of the body. Input signals are processed to synthesize one or more signals substantially corresponding to an unsynthesized signal or signals that would be produced by a further chest electrode or electrodes, if each were used on the body at a chest position or positions other than the conventional positions. The synthesized signal or signals is or are then provided as an output to the electrocardiograph. The apparatus may include provision which selectively permits synthesized or unsynthesized signals to be provided as an output to the electrocardiograph. A method of monitoring heart activity of a human body includes the steps of attaching chest electrodes at chest positions V1, V2, V3, V4, V5 and V6 of the body, attaching limb electrodes at positions RA, LA and LL of the body, sensing voltage signals produced by such electrodes in response to heart activity; and, synthesizing from the sensed signals a voltage signal substantially corresponding to a voltage signal that would be produced by a further chest electrode, if a further chest electrode was used.

5,711,304
Page 2

17 Claims, 3 Drawing Sheets

5,711,304

SIGNAL PROCESSING APPARATUS AND METHOD FOR ADDING ADDITIONAL CHEST LEADS TO THE 12-LEAD ELECTROCARDIOGRAM WITHOUT ADDITIONAL ELECTRODES

This application is a continuation of application Ser. No. 08/385,817, filed on Feb. 9, 1995.

FIELD OF THE INVENTION

This invention relates to electrophysiology and, in particular, to signal processing apparatus used in electrocardiography.

BACKGROUND TO THE INVENTION

In order to better understand the background and concept of the present invention it is desirable to describe the terminology of electrocardiography and vectorcardiography.
Electrocardiography The term electrocardiogram ("ECG") was coined by Einthoven (see W. Einthoven, G. E. Fahr, A. DeWart, *On the Direction and Manifest Size of the Variations of Potential in the Human Heart and on the Influence of the Position of the Heart on the Form of the Electrocardiogram* (translation), Am. Heart J. 40:163, 1950). It refers to a plot against time of the varying potential differences produced by the heart between body surface electrodes, at specified locations. The conventional 12-lead ECG is a set of 12 such plots identified as leads I, II, III, aVR, aVL, aVF, V1, V2, V3, V4, V5 and V6, recorded from electrodes on the right arm (RA), left arm (LA), left leg (LL), and on the chest: see FIG. 1. A 10th electrode is usually placed on the right leg (RL) to serve as a ground, to reduce 60-cycle noise. However, placement of a ground electrode on the right leg is merely a matter of convenience. Other ground electrode positions may be used and, while the designation RL implies a ground electrode, it does not mean that the electrode is necessarily placed on the right leg. Herein, and following common practice, RA is abbreviated to R, LA is abbreviated to L, LL is abbreviated to F (for foot), and RL is abbreviated to G (for ground).

Note that the term "lead" has a dual meaning and must be taken in its proper context. Sometimes it refers to a wire connected to a patient. Sometimes it refers to a tracing. The following account requires close attention to various references of potential used in electrocardiography, yet this is difficult because an inconsistent terminology has evolved. Time varying potential differences will be indicated by the lower case symbol "v" with subscripts to indicate polarity—the first indicating the positive pole of the measuring device, the second indicating the negative pole or reference potential.

Einthoven's original leads were I, II and III tracings of the voltages between LA and RA, LL and RA, and LL and LA, respectively, with the convention that upward deflections resulted when the leading member of each of the foregoing electrode pairs became positive with respect to the other. Herein, the time varying voltage or signal giving rise to the lead I tracing is denoted as $v_{LR}$, that for lead II as $v_{FR}$, and that for lead III as $v_{FL}$. (Modern electrocardiographs employ differential amplifiers to reject common-mode electrical noise, so $v_{LR}$ is given as $V_{LG} - V_{RG}$, etc.)

The chest leads V1—V6 were introduced by Wilson (see F. N. Wilson, F. D. Johnston, A. G. MacLeod, P. S. Barker, *Electrocardiograms that Represent the Potential Variations of a Single Electrode*, Am. Heart J. 9:447, 1934), who referred to the chest electrode as the exploring electrode. An upward deflection occurred when the exploring electrode became positive with respect to what he thought of as a neutral reference: the "central terminal" formed from the tie point of three equal resistors from the RA, LA and LL electrodes. Herein, Wilson's central terminal WCT is denoted by W. Thus, the signals recorded as V1 to V6 will be $v_{1W}$ to $v_{6W}$.

Since they use WCT as a reference, leads V1–V6 are called unipolar leads, whereas leads I, II and III are called bipolar leads. The early electrocardiographs were single-channel devices, hence the chest leads of the ECG were recorded in sequence, the exploring electrode being moved to record the various chest leads sequentially. Subsequently, the exploring electrode was also placed on the limbs to record the unipolar limb leads VR, VL and VF. The signals recorded as these leads were $v_{RW}$, $v_{LW}$, and $v_{FW}$, respectively. Goldberger observed that the central terminal resistor connected to the explored limb partly shunted the signals, so he removed it thereby augmenting the signals (see E. Goldberger, *A Simple, Indifferent Electrocardiographic Electrode of Zero Potential and Technique of Obtaining Augmented, Unipolar, Extremity Leads*, Am. Heart J. 23:483, 1942). The "augmented" unipolar limb leads aVR, aVL and aVF complete the set of 12 leads, or tracings, in the 12-lead ECG.

In electrocardiography texts, Einthoven's triangle is commonly used to show the relationships between limb-lead electrodes and tracings. To enable a better understanding of the terminology used herein, Einthoven's triangle is shown on the left in FIG. 2 together with its comparable representation on the right which adopts the terminology. FIG. 2 shows that Einthoven's law, viz.

lead II=lead I+lead III is equivalent to Kirchoffs voltage law, viz.

$V_{LR} + V_{FL} + V_{RF} = 0$.

One may go on to show that only two channels of information are required to produce all six limb leads of the 12-lead ECG. This is made use of in today's electrocardiographs which record only eight channels of information, two for the limb leads and six for the chest leads. A modern electrocardiograph typically has 10 lead wires in the cable going to the patient, records the ECG in 8 channels of information, and produces 12 ECG tracings.

Vectorcardiography

The cyclic pattern of body surface potentials that results from the heart's cycle of electrical activation and recovery is a manifestation of an electric field in the body. Such field can be approximated by a mathematical model that represents the heart as a current dipole of varying direction and magnitude. This is a three-dimensional vector quantity and is called the heart vector.

The heart vector changes from instant to instant. According to the lead vector concept of Burger and van Milaan, for every electrode position on the body surface there is a lead vector (see H. E. Burger, J. B. van Milaan, *Heart Vector and Leads*, Brit. Heart J. 10:229, 1948). The scalar product of the lead vector and the heart vector gives the instantaneous potential in the unipolar ECG lead for that electrode position. The difference between the two unipolar lead vectors of two body surface electrodes gives the bipolar lead vector whose scalar product with the heart vector yields the instantaneous potential of the bipolar ECG lead between the two electrodes.

The heads of the unipolar lead vectors for all points on the body surface define an image surface. Frank (see E. Frank,

*The Image Surface of a Homogenous Torso*, Am. Heart J. 47:757, 1954) experimentally mapped the image surface of one individual and used the lead vector concept to design a system of eight electrodes, with appropriate lead wires and resistors (see E. Frank, *An Accurate, Clinically Practical System for Spatial Vectorcardiography*, Circ. Res. 3:243, 1955), known as the Frank lead system. Except for RL and LL, the electrode positions of the Frank lead system differ from the 10 used in the conventional ECG. The outputs of the Frank lead system are three voltage signals known as x, y and z, because they correspond to the rectangular coordinates of the heart vector, times a scaling factor. These signals can be graphed as x, y and z orthogonal ECG tracings, but a more common practice is to make xy, xz and yz plots or "loops" known as vectorcardiograms (VCGs) in the frontal, transverse and sagittal planes of the subject.

VCGs have not gained popularity, but they have provided valuable insight into the inter-relationships between the various ECG tracings, which are essentially projections of the VCG loops onto lines representing the approximate directions of the lead vectors. Such projections can be made in software or hardware. This was done when Dower et al. described the derivation (i.e. synthesis) of the 12-lead ECG from the xyz signals of the Frank lead system (see G. E. Dower, H. B. Machado, J. A. Osborne, *On Deriving the Electrocardiogram from Vectorcardiographic Leads*, Clin. Cardiol. 3:87:1980). The resulting derived or synthesized ECG ("ECGD") matches the ECG closely enough for most clinical purposes. But, the match is not exact partly because the representation of the heart by a current dipole is only about 90 per cent correct. The reason for synthesizing the ECG as the ECGD, rather than recording it directly from the conventional electrode positions, was to save the technician the effort of applying two lead systems when both ECGs and VCGs were required. Edenbrandt and Pahlm avoided dual systems by synthesizing the Frank xyz signals from the conventional ECG lead signals by using a matrix that was the inverse of that which Dower used to synthesize the 12-lead ECGD from the xyz signals of Frank (see L. Edenbrandt, O. Pahlm, *Vectorcardiogram Synthesized From a 12-lead ECG: Superiority of the Inverse Dower Matrix*, J. Electrocardiol. 21:361, 1988). They termed the new matrix the inverse Dower matrix.

U.S. Pat. No. 4,850,370 entitled *Method and Apparatus for Sensing and Analyzing Electrical Activity of the Human Heart*, granted to G. E. Dower on Jul. 25, 1989, describes a method and apparatus for producing xyz vectorcardiographic signals, electrocardiographic signals corresponding to the lead signals of a 12-lead electrocardiogram, or both, utilizing four electrode positions on the chest of a patient. With a reduced number of electrodes, the method and apparatus described could be used in circumstances where a conventional system of 10 electrodes would be difficult or impractical.

Extra Chest Leads

Although the number of electrode positions on the chest for recording the 12-lead ECG is typically six, other positions such as V7, V8, V9, V3R, V4R and V5R have been used occasionally: see FIG. 3. These positions can be helpful in the diagnosis of certain conditions, e.g. infarctions on the posterior or right aspects of the heart. However, increasing the number of electrodes from 10 to 16 can be a burdensome routine.

Accordingly, a primary object of the present invention is to provide apparatus for producing one or more extra chest leads without the use of extra electrodes.

A further object of the present invention is to provide new and improved apparatus which, utilizing the system of a conventional 12-lead ECG and its conventional electrode positions, enables health care professionals to substantially see the ECG patterns that would arise from one or more other electrode positions around the chest of a subject's body.

A further object of the present invention is that the apparatus be easily usable in conjunction with existing or conventional electrocardiographs.

SUMMARY OF THE INVENTION

In a broad aspect of the present invention, there is provided signal processing apparatus for use with an electrocardiograph monitoring activity of the human heart, the apparatus including input means for receiving input signals from chest electrodes positioned at conventional positions V1, V2, V3, V4, V5 and V6 and limb electrodes positioned at conventional positions RA, LA and LL. Signal processing means is operatively connected to such input means for synthesizing a signal substantially corresponding to the synthesized signal that would be provided by a further chest electrode, if such a further electrode was used on the body at a chest position other than the conventional positions. The apparatus further includes signal output means for providing the synthesized signal as an output to the electrocardiograph.

The synthesized signal may be a signal corresponding to a signal from the group consisting of chest lead signals V3R, V4R, V5R, V7, V8 and V9.

In a preferred embodiment of the present invention, the apparatus includes means for providing unsynthesized signals as an output to the electrocardiograph from the signal output means. Further, the preferred embodiment includes signal selection means for selectively directing to the output means unsynthesized signals corresponding to the input signals from the conventionally positioned limb and chest electrodes, or the synthesized signal. The input means may also include means for receiving an input signal from a conventional ground electrode at position RL (which, as noted above, is a position of convenience and not necessarily the right leg).

The signal selection means may comprise a switch switchable between a first position at which the unsynthesized signals are directed to the output means and a second position at which the unsynthesized signal is directed to the output means.

Further, it is contemplated that apparatus in accordance with the present invention will preferably be structured not merely to unsynthesize a single signal corresponding to a single further chest electrode, but to derive two or more signals corresponding to two or more further chest electrode positions. The derived signals may correspond to two or more signals from the group of chest lead signals V3R, V4R, V5R, V7, V8 and V9.

The output of apparatus in accordance with the present invention may be simply connected to the input of a conventional electrocardiograph. When synthesized signals are selected at the output, the electrocardiograph is responsive to produce tracings of leads I, II, III, aVR, aVL, aVF, V1, V2, V3, V4, V5 and V6 of a 12-lead ECG. When synthesized signals are selected at the output, the electrocardiograph is responsive to substantially produce tracings of leads that could be produced directly with additional chest electrodes.

With the foregoing selection feature, the 12 leads of a conventional ECG are preserved in an original unsynthesized form. They are uncompromised by the approximation implicit in the heart vector concept. Yet, with the present invention, synthesized ECG leads corresponding to those which would arise from other electrode sites around the chest can be observed without adding significantly to the cost of the procedure for a conventional 12-lead ECG. In relation to the interpretation of results, both as to the conventional 12 leads and as to additional synthesized leads, the selection feature is particularly advantageous because it enables comparison with current and previously recorded conventional ECGs with the knowledge that any observed discrepancies will not have arisen from a synthesis procedure.

In accordance with another aspect of the present invention, there is provided a method of monitoring heart activity of a human body comprising the steps of attaching chest electrodes at chest positions V1, V2, V3, V4, V5 and V6 of the body, attaching limb electrodes at positions RA, LA and LL of the body; sensing voltage signals produced by the electrodes in response to the heart activity; and, synthesizing from the sensed signals a voltage signal substantially corresponding to the voltage signal that would be produced by a further chest electrode, if such a further chest electrode was used on the body at a chest position other than chest positions V1 to V6. In a preferred embodiment the synthesized signal is a signal substantially corresponding to a signal that would be produced by a further chest electrode located on the body at a position selected from the group consisting of chest positions V3R, V4R, V5R, V7, V8 and V9.

The foregoing and other features and advantages of the present invention will now be described with reference to the drawings.

DETAILED DESCRIPTION

Figure 1:
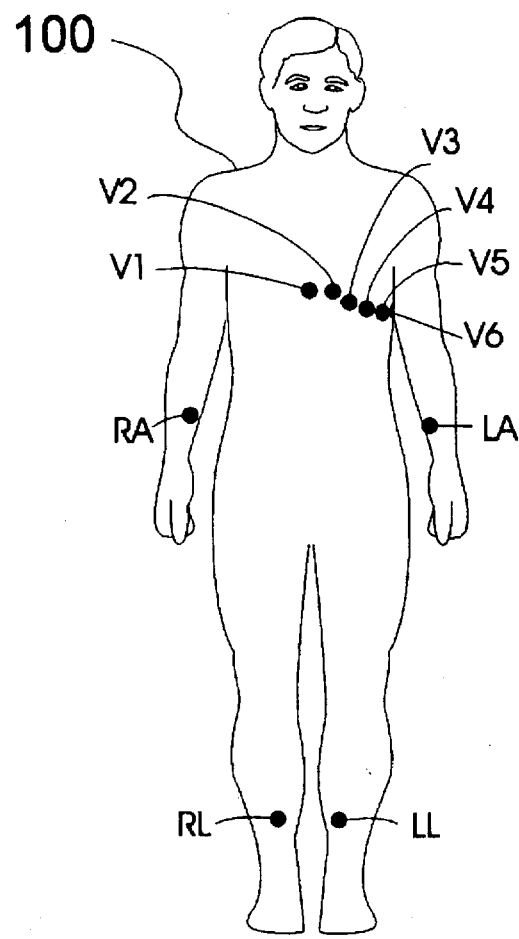
FIG. 1 illustrates a human body with conventional ECG electrode positions.
Figure 3:
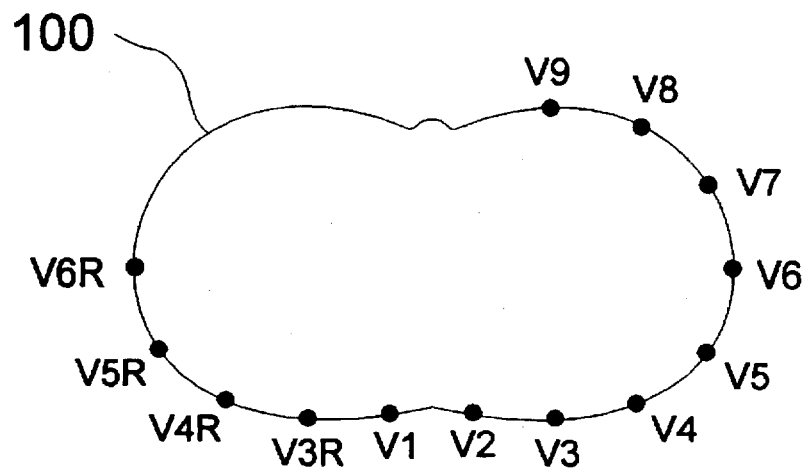
Figure 5:
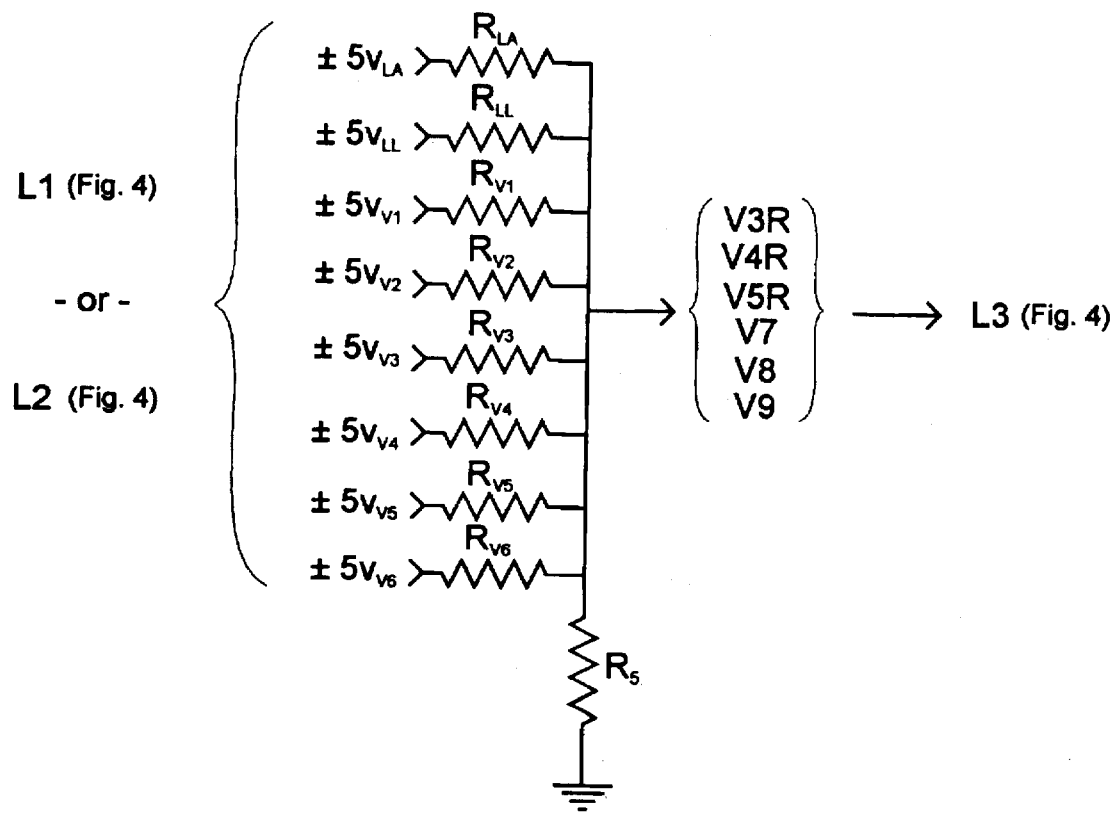
FIG. 5, which is on the same sheet of drawings as FIG. 2, is a circuit diagram of a resistor network which interconnects with the circuitry shown in FIG. 4.
Figure 4:
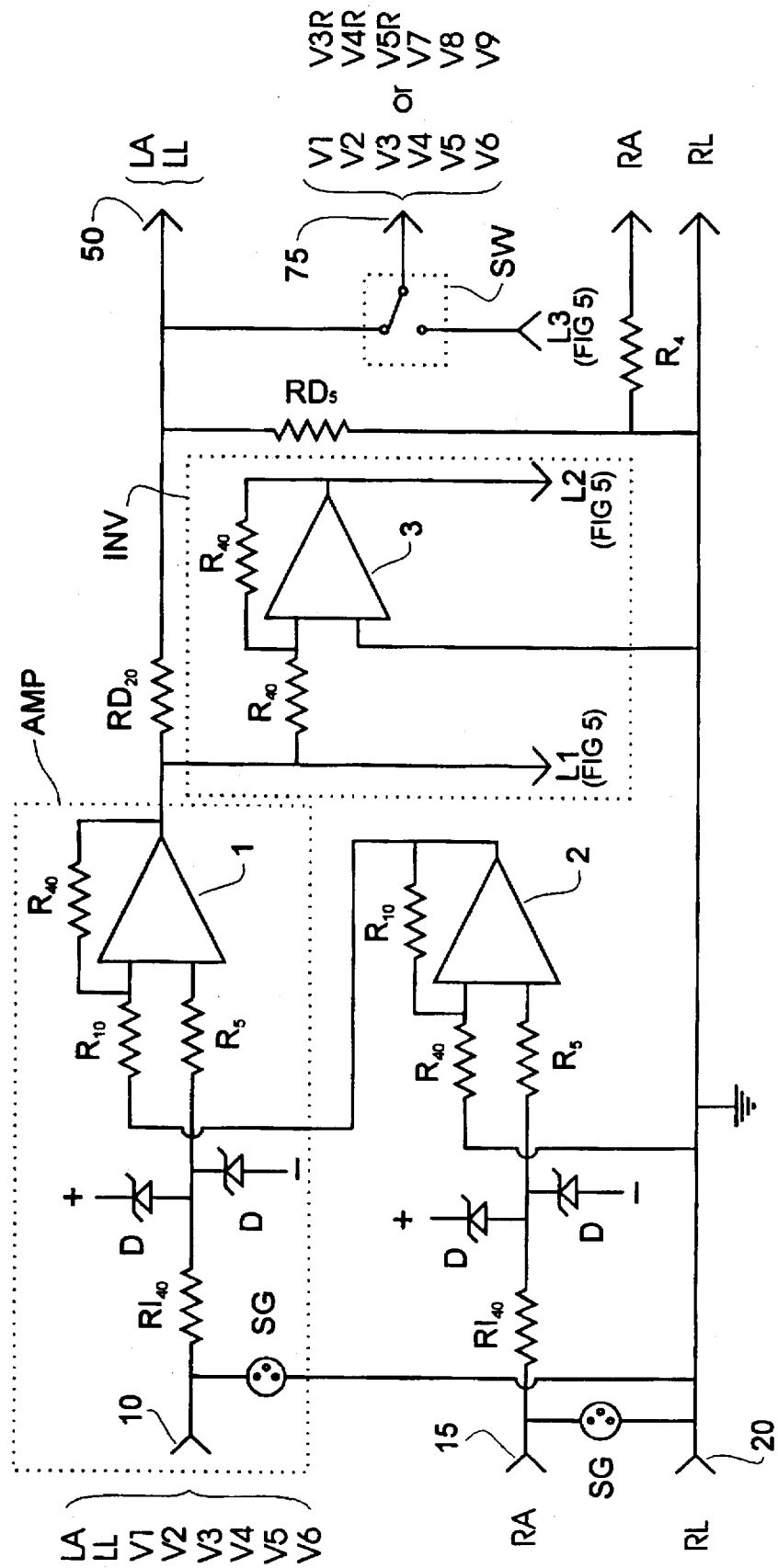
FIG. 4 is a circuit diagram of signal processing circuitry forming part of an apparatus in accordance with the present invention.

The apparatus shown in FIGS. 4 and 5 illustrates signal processing circuitry which forms part of an apparatus designed to receive input signals from electrodes at conventional positions LA, LL, V1, V2, V3, V4, V5, V6, RA and ground RL of body 100 shown in FIG. 1, and to provide as an output unsynthesized signals corresponding to the signals from such conventionally positioned electrodes, or synthesized signals substantially corresponding to signals that would be produced from electrodes at chest positions V3R, V4R, V5R, V7, V8 and V9 shown in FIG. 3. The output is provided to a conventional electrocardiograph (not shown). When such synthesized signals are provided as an output, they are provided to the exclusion of the unsynthesized signals from the electrodes at positions V1 to V6; not to the exclusion of all unsynthesized signals. The unsynthesized signals from electrodes at positions LA, LL, RA and RL will continue to appear.

Only part of the apparatus is shown in FIGS. 4 and 5 because the remaining part is generally repetitive of that which is shown. Thus, while FIG. 4 illustrates an input amplifier unit AMP with a single input 10, the complete apparatus includes eight of such units; one for an input from each of the eight electrodes at positions LA, LL, V1, V2, V3, V4, V5 and V6. Each unit incorporates basic amplifier circuitry comprising a high input gain operational amplifier 1, input resistors $R_5$ and $R_{10}$, and feedback resistor $R_{40}$. As well, each unit incorporates at its input a spark gap SG, resistor $RL_{40}$ and zener diodes D to protect against input overvoltages such as may occur if the apparatus is wired to a heart patient during defibrillation.

In the example of the present embodiment, it may be noted that actual resistance values for the resistors shown in FIG. 4 correspond in kilohms to their labelled subscripts. Thus, in the case of amplifier unit AMP, $R_5$ indicates a 5 kilohm resistor, $R_{10}$ indicates a 10 kilohm resistor, and $R_{40}$ indicates a 40 kilohm resistor. The same is true for all other resistors shown in FIG. 4.

FIG. 4 also shows an input 15 for an input from the electrode at position RA in FIG. 1, and an input 20 for a ground input from the electrode at position RL in FIG. 1. The circuitry through which signals received at input 15 are processed includes a high input gain operational amplifier 2, input resistors $R_5$ and $R_{40}$, and feedback resistor $R_{10}$. As in the case of each input amplifier unit AMP, the circuitry after input 15 incorporates a spark gap SG, resistor $RL_{40}$ and zener diodes D.

Figure 2:
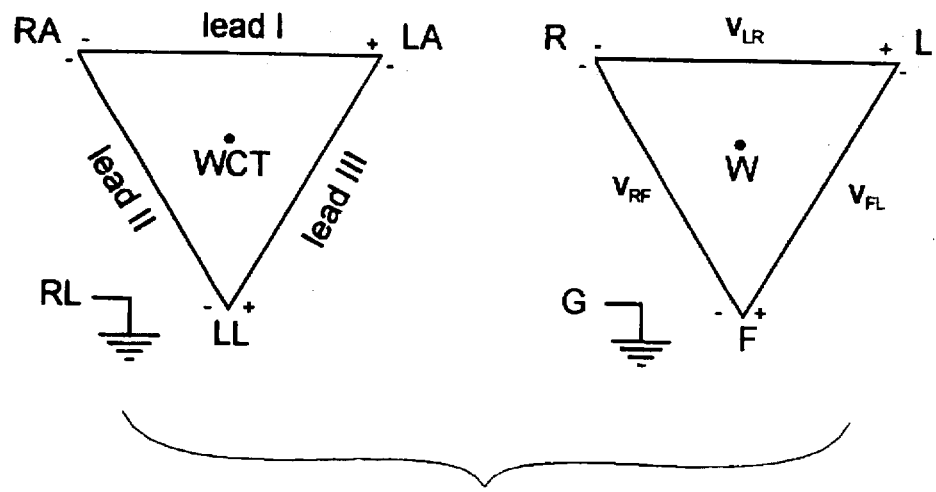
FIG. 2 graphically illustrates terminology used herein with a drawing of Einthoven's triangle FIG. 3, which is on the same sheet of drawings as FIG. 1, is a transverse section of the chest illustrating chest leads V3R, V4R, V5R, V6R, V7, V8 and V9 in addition to chest leads V1 to V6 shown in FIG. 1

The signal between RA and RL in FIG. 4, i.e. $v_{RG}$ in FIG. 2, is amplified 5/4 times by amplifier 2 and fed through $R_{10}$ at the inverting input of amplifier 1 which amplifies the signal by minus 4 times to give $-5v_{RG}$. The signals between each of the eight inputs to the eight AMPs and RL become $5v_{LG}$, $5v_{FG}$, $5v_{1G}$, $5v_{2G}$, $5v_{3G}$, $5v_{4G}$, $5v_{5G}$ and $5v_{6G}$. With $-5v_{RG}$ added to each, they become, respectively, $5v_{LR}$, $5v_{FR}$, $5v_{1R}$, $5v_{2R}$, $5v_{3R}$, $5v_{4R}$, $5v_{5R}$ and $5v_{6R}$. Thus, the outputs from the eight AMPs, each leading to a corresponding line L1, give the signals between the LA, LL, V1, V2, V3, V4, V5 and V6 electrodes and the RA electrode, each increased 5-fold and referenced to RL. Common mode signals, i.e. signals common to both the LA to V6 electrodes and to RA, all appearing with respect to RL, cancel.

The signals on lines L1 are then reduced to their original size by voltage dividers formed by $RD_{20}$ and $RD_5$ (only one of which is shown in FIG. 4). The $v_{LR}$ and $v_{FR}$ signals are fed directly to associated outputs 50 (one for LA, one for LL—only one of which is shown in FIG. 4). The other signals, $v_{1R}$ to $v_{6R}$, are fed to switch SW which is a 6-pole, 2-position switch leading to six outputs 75. Only one of outputs 75 is shown in FIG. 4, and may be considered as the output for any one of V1, V2, V3, V4, V5 or V6 when switch SW is in the upward throw position indicated in FIG. 4.

It will be understood that the signals from the electrodes at positions V1 to V6 which appear at outputs 75 when switch SW is in the upward throw position shown in FIG. 4 are unsynthisized signals. When switch SW is in this position, the signals from outputs 50, which are also unsynthesized signals, and the signals from outputs 75 may be fed directly to a conventional electrocardiograph to produce a conventional 12-lead ECG.

The RA output in the apparatus of FIG. 4 arises directly from the apparatus ground which is seen as RL at the input to the apparatus. To understand this arrangement, imagine that the RL electrode is placed on the right arm. (The location of the right leg electrode does not affect the 12-lead ECG). Now, consider the signal from a patient between LA and RA. This double-ended signal referred or measured with reference to RL has been converted to a single-ended signal referred to RA. Thus, the input signals are $v_{LG}$ and $v_{RG}$, whereas the output signal is $v_{LR}$, which an electrocardiograph will plot as the lead I tracing. Similarly, all inputs are referred to RL whereas all outputs are referred to RA. Note, however, that the pattern of potential differences among the inputs, including RA, is reproduced among the outputs, including RA. Consequently, an electrocardiograph attached to the outputs will respond as if it were attached to the inputs. Its output will not be affected by placing the RL electrode on the right arm instead of the right leg. Note that the impedance to RL of the outputs are due to $RD_{20}$ in parallel with $RD_5$, i.e. 4 units (in practice, 4 kilohms). To match this impedance, there is resistor $R_4$ at the RA output.

The circuitry that produces synthesized signals substantially corresponding to signals that would be produced from electrodes at chest positions V3R, V4R, V5R, V7, V8 and V9 comprises seven inverter units INV, only one of which is shown in FIG. 4, and six resistor networks like that shown in FIG. 5. Each inverter unit comprises an operational amplifier 3 wired with input and feedback resistors $R_{40}$ to produce a unity gain signal inversion.

As indicated in FIG. 5, each of the six resistor networks is associated with one of the six desired synthesized signals. They receive inputs either from a line L1 or a line L2 shown in FIG. 4. A derived signal is produced as an output on a line L3 in FIG. 5—and this signal is also the input along the same line to a corresponding downward throw position of switch SW in FIG. 4. When switch SW is in the downward throw position, the synthesized signals will appear at outputs 75 and may be fed directly to a conventional electrocardiograph to produce tracings of leads V3R, V4R, V5R, V7, V8 and V9. The signals that will do this are $v_{(3R)R}$, $v_{(4R)R}$, $v_{(5R)R}$, $v_{7R}$, $v_{8R}$ and $v_{9R}$, i.e. they are referred to RA, not WCT.

It will be readily apparent from FIG. 4 that unsynthesized signals will continue to appear at the LA and LR outputs 50, and the RA and LL outputs, when switch SW is in its downward throw position.

The synthesized signals substantially correspond to unsynthesized signals that could be obtained directly from further chest electrodes positioned on the chest of body 100 at positions V3R, V4R, V5R, V7, V8 and V9 indicated in FIG. 3. In performing the synthesis, inverter units INV would not be used but for the fact that some of the resistor values in the network of FIG. 5 become negative in some cases. If this were not so, and if all resistors were determined to have positive resistance values, then all inputs to the resistor network of FIG. 5 could be taken from a line L1 in FIG. 4. However, as some resistors were determined to have negative resistance values, the equivalent of a negative resistance was achieved by assuming a positive value and inverting the signal input.

In more detail, Table 1 below shows calculated resistance values for a resistor network associated with each synthesized lead V3R, V4R, V5R, V7, V8 and V9. Some of the values are positive values; some are negative. A negative value does not mean negative resistance. Rather, it indicates that the input to the resistor should come from line L2 in FIG. 4 instead of line L1.

TABLE 1

| | $R_{LA}$ | $R_{LL}$ | $R_{V1}$ | $R_{V2}$ | $R_{V3}$ | $R_{V4}$ | $R_{V5}$ | $R_{V6}$ |
|---|---|---|---|---|---|---|---|---|
| V3R | −120 | 70 | 88 | 111 | 665 | −341 | −243 | −264 |
| V4R | −171 | 94 | 138 | 193 | 11165 | −444 | −392 | −485 |
| V5R | −190 | 87 | 201 | 443 | −558 | −486 | −888 | −6080 |
| V7 | 348 | 84 | −118 | −100 | −328 | 124 | 73 | 67 |
| V8 | 704 | 87 | −149 | −114 | −259 | 179 | 93 | 83 |
| V9 | 10818 | 77 | −164 | −108 | −179 | 263 | 107 | 89 |

Resistance values are stated in kilohms.

Note that all resistance values for RLL are positive. Thus, no inverter INV is required for $v_{LL}$.

The apparatus shown in FIGS. 4 and 5 effectively combines the idea of the inverse Dower matrix with the idea of obtaining extra chest leads without applying more electrodes. When the apparatus is interposed between a patient and an electrocardiograph, an 18-lead ECG can be obtained routinely, without significant extra work by a technician.

However, as it will not be obvious, the following description will serve to explain how the resistance values shown in Table 1 were determined.

Derivation of Lead Vectors for the Extra Leads

The locations of the electrodes for the extra leads V3R, V4R, V5R, V6R, V7, V8 and V9 are shown in transverse section of the chest in FIG. 3. The coordinates of the positions to which these map on Frank's image surface give the lead vectors for these locations. Because Frank did not define the image surface for these positions, the coordinates were obtained by visual interpolation from two-dimensional projections of image surface contours. They were found to be as follows:

$$V3R=-92i+10j-39k$$

$$V4R=-84i-5j-7k$$

$$V5R=-77i-6j+10k$$

$$V6R=-73i-8j+22k$$

$$V7=-70i-26j+74k$$

$$V8=-44i-25j+85k$$

$$V9=15i-17j+92k$$

where i, j and k are orthogonal unit vectors.

Frank used xyz coordinates instead of ijk coordinates, but this can cause confusion because the heart vector It is conveniently expressed as:

$$H=xi+yj+zk$$

whose scalar product with a lead vector L=ai+bj+ck gives the signal in that lead due to the heart as:

$$H \cdot L=ax+by+cz$$

where x, y and z are functions of time and a, b and c are functions of position, tissue conductivity, and geometry. Another term for lead vector L is transfer impedance.

The required unipolar lead chest signals are referred to WCT, but Frank did not choose this as the reference for his image surface. From his diagrams, the lead vector for WCT is:

$$L_{WCT}=-15i-12j+28k$$

which must be subtracted from the lead vectors given above to obtain the following unipolar lead vectors:

$L_{(3R)W} = -77i + 22j - 67k$ $L_{(4R)W} = -69i + 7j - 35k$ $L_{(5R)W} = -62i + 6j - 18k$ $L_{(6R)W} = -58i + 4j - 6k$ $L_{7W} = -85i - 14j + 46k$ $L_{8W} = -59i - 13j + 57k$ $L_{9W} = -30i - 5j + 64k$

Dividing these equations by Frank's scaling factor of 136 and forming the scalar product with the heart vector gives the unipolar lead signals for each of the electrode positions.

$v_{(3R)W} = -0.566x + 0.162y - 0.493z$ $v_{(4R)W} = -0.507x + 0.051y - 0.257z$ $v_{(5R)W} = -0.456x + 0.044y - 0.132z$ $v_{(6R)W} = -0.426x + 0.029y - 0.044z$ $v_{7W} = 0.625x - 0.103y + 0.338z$ $v_{8W} = 0.434x - 0.096y + 0.419z$ $v_{9W} = 0.221x - 0.037y + 0.471z$

Earlier work on the coefficients given in the Dower matrix (see *On Deriving* . . . op. cit.) refers to improvement on the coefficients obtained from Frank's image surface data as a result of a study of several hundred cases. The lead vectors of the resulting Dower matrix were plotted on an Aitoff equal area projection. On the projection, the limb-lead vectors lay approximately along the equator, and the chest vectors lay approximately along the zero and 180° meridians.

The lead vectors for the extra leads were then transformed into spherical coordinates and added to the Aitoff projection. It turned out that there was some unevenness in the angular spacing of the new lead vectors, but this was reduced by slightly moving the vectors. The rationale for so doing was that the new lead tracings may be related by the cardiologist to the corresponding vectorcardiograms (*On Deriving* . . . op. cit. FIG. 5). This visual exercise would be less satisfactory if the angular spacing between some of the new lead vectors were uneven, because the conceptual application of the present invention is to obtain different views of the heart, electrically speaking, when looking for evidence of myocardial ischemia or infarction. Lacking experimental data at this time, this process was used to obtain extra chest leads of potential clinical value.

The spherical coordinates thus obtained from the Aitoff projection did not include magnitudes because the magnitude coordinate (radius) is not represented in the projection. Accordingly, the magnitude coordinates were taken from, or interpolated from, the magnitudes of the lead vectors for the extra leads obtained from Frank's image surface after transformation from rectangular to spherical coordinates. The resulting spherical coordinates were transformed to rectangular coordinates to give the following:

$v_{(3R)W} = -0.566x + 0.164y - 0.490z$ $v_{(4R)W} = -0.507x + 0.053y - 0.289z$ $v_{(5R)W} = -0.463x + 0.041y - 0.107z$ $v_{(6R)W} = -0.425x + 0.010y - 0.022z$ $v_{7W} = 0.587x - 0.031y + 0.412z$ $v_{8W} = 0.376x + 0.411z$ $v_{9W} = 0.221x + 0.473z$

It will be understood that the embodiment of the invention shown in FIGS. 4 and 5 represents an analog implementation. For this implementation, the extra leads are limited to six, viz. V3R, V4R, V5R, V7, V8 and V9, to replace the six chest leads recorded by a conventional electrocardiograph. Consequently, the $v_{(6R)W}$ signal is not used, although there is no theoretical reason why not.

The above equations give signals with respect to WCT which is not the output reference in the circuit of FIG. 4. In FIG. 4, the output reference is RA. (When connected to a conventional electrocardiograph, the electrocardiograph will establish the WCT reference.). To change the reference from WCT to RA, i.e. to make $v_{RW} = 0$, $v_{RW}$ is subtracted from each equation. Working from the triangle diagram in FIG. 2, it can readily be shown that:

$v_{RW} = -(v_{LR} + v_{FR})/3 = -(v_I + v_{II})/3$

Since, from the published Dower matrix:

$v_I = 0.632x - 0.235y + 0.059z$ and $v_{II} = 0.235x + 1.066y - 0.132z$ therefore:

$v_{RW} = -0.289x - 0.0277y + 0.024z$ and it follows that:

$v_{(3R)W} = -0.277x + 0.441y - 0.514z$ $v_{(4R)W} = -0.218x + 0.330y - 0.313z$ $v_{(5R)W} = -0.174x + 0.318y - 0.131z$ $v_{7W} = 0.876x + 0.308y + 0.388z$ $v_{8W} = 0.665x + 0.277y + 0.387z$ $v_{9W} = 0.510x + 0.277y + 0.449z$ \hfill (1)

Herein, the matrix of coefficients from the set of equations (1) will be referred to as the analog extra lead matrix because it is convenient for analog implementation.

The published Dower matrix was intended for software implementation. Consequently, the published inverse Dower matrix was similarly intended. This means that the inverse Dower matrix cannot be used directly on the electrode signals coming from a patient because there is no common reference. Its inputs $v_I$ and $v_{II}$ are referred to RA, whereas its inputs $v_{V1}$ to $v_{V6}$ are referred to WCT. Following the convention adopted herein, the inputs are $v_{LR}$, $v_{FR}$, $v_{1W}$, $v_{2W}$, $v_{3W}$, $v_{4W}$, $v_{5W}$ and $v_{6W}$. For analog implementation, and although it would be possible with suitable circuitry to generate the $v_{1W}$ to $v_{6W}$ signals, it is simpler to calculate and use a new matrix which may be referred to as an analog inverse matrix. For this purpose, the relevant equations of the published Dower matrix are:

$v_{LR} = 0.632x - 0.235y + 0.059z$ $v_{FR} = 0.235x + 1.066y - 0.132z$ $v_{1W} = -0.515x + 0.157y - 0.917z$ $v_{2W} = 0.044x + 0.164y - 1.387z$ $v_{3W} = 0.882x + 0.098y - 1.277z$ $v_{4W} = 1.213x + 0.127y - 0.601z$ $v_{5W} = 1.125x + 0.127y - 0.086z$ $v_{6W} = 0.831x + 0.076y + 0.230z$

Following the same procedures as used to obtain the analog extra lead matrix, and subtracting $v_{RW}$ from all but the first two of the above equations (which already use RA as a reference), gives the following set of equations the coefficients of which give the Dower matrix when all inputs are referred to RA:

$v_{LR} = 0.632x - 0.235y + 0.059z$ $v_{FR} = 0.235x + 1.066y - 0.132z$ $v_{1R} = -0.226x + 0.434y - 0.941z$ $v_{2R} = 0.333x + 0.441y - 1.411z$ $v_{3R} = 1.171x + 0.375y - 1.301z$ $v_{4R} = 1.502x + 0.404y - 0.625z$ $v_{5R} = 1.414x + 0.404y - 0.110z$ $v_{6R} = 1.120x + 0.353y + 0.206z$     (2)

If the coefficient matrix from the foregoing set of equations (2) is defined as A, and if $A^T A$ is defined as M where $A^T$ is the transpose of A, then, following Edenbrandt and Pahlm (op. cit.), the inverse Dower matrix when referred to RA is $M^{-1} A^T$ where $M^{-1}$ is the inverse of M. More particularly:

|       |     | X     | Y     | Z     |
|-------|-----|-------|-------|-------|
| $\underline{A} =$ | LR  | .632  | -.235 | +.059 |
|       | FR  | .235  | 1.066 | -.132 |
|       | CR1 | -.226 | .434  | -.941 |
|       | CR2 | .333  | .441  | -1.411 |
|       | CR3 | 1.171 | .375  | -1.301 |
|       | CR4 | 1.502 | .404  | -.625 |
|       | CR5 | 1.414 | .404  | -.110 |
|       | CR6 | 1.120 | .353  | .206  | and,

|       |   | LR   | FR    | CR1   | CR2    | CR3    | CR4   | CR5   | CR6   |
|-------|---|------|-------|-------|--------|--------|-------|-------|-------|
| $\underline{A^T} =$ | X | .632 | .235  | -.226 | .333   | 1.171  | 1.502 | 1.414 | 1.120 |
|       | Y | .235 | 1.066 | .434  | .441   | .375   | .404  | .404  | .353  |
|       | Z | .059 | -.132 | -.941 | -1.411 | -1.301 | -.625 | -.110 | .206  |

Note that the labelling for the matrices A and $A^T$ uses "C" as an abbreviation for "chest". Thus, in accordance with the general convention used herein, the combination "CR" means chest to right arm.

The product $A^T A$ then may be calculated as:

$$\underline{M} = \begin{matrix} 7.498 & 2.163 & -2.638 \\ 2.163 & 2.166 & -1.897 \\ -2.638 & -1.897 & 5.035 \end{matrix} \quad \text{and,} \quad \underline{M^{-1}} = \begin{matrix} .193 & -.156 & .043 \\ -.156 & .815 & .225 \\ .043 & .225 & .306 \end{matrix}$$

Then, the inverse Dower matrix referred to RA is:

|            |   | LR    | FR    | CR1   | CR2   | CR3   | CR4   | CR5   | CR6   |
|------------|---|-------|-------|-------|-------|-------|-------|-------|-------|
| $M^{-1}A^T =$ | X | .161  | -.126 | -.151 | -.064 | .113  | .201  | .206  | .170  |
|            | Y | -.277 | .802  | .177  | -.011 | -.170 | -.046 | .084  | .160  |
|            | Z | -.008 | .210  | -.200 | -.318 | -.264 | -.036 | .118  | .190  |

Continuing, the product of $M^{-1} A^T$ with the analog extra lead matrix:

|      | X     | Y    | Z     |
|------|-------|------|-------|
| CR3R | -.277 | .441 | -.514 |
| CR4R | -.218 | .330 | -.313 |
| CR5R | -.174 | .318 | -.131 |
| CR7  | .876  | .308 | .388  |
| CR8  | .665  | .277 | .387  |
| CR9  | .510  | .277 | .449  |

(see set of equations (1) above)

then gives the following matrix V of coefficients for output voltages to be fed to the electrocardiograph:

|           |      | LR    | FR   | v(CR1) | v(CR2) | v(CR3) | v(CR4) | v(CR5) | v(CR6) |
|-----------|------|-------|------|--------|--------|--------|--------|--------|--------|
| $\underline{V} =$ | CR3R | -.163 | .281 | .223   | .176   | .029   | -.057  | -.081  | -.074  |
|           | CR4R | -.124 | .226 | .154   | .110   | .002   | -.048  | -.054  | -.044  |
|           | CR5R | -.115 | .249 | .109   | .049   | -.039  | -.045  | -.025  | -.004  |
|           | CR7  | .053  | .218 | -.155  | -.183  | -.056  | .148   | .252   | .272   |
|           | CR8  | .027  | .220 | -.129  | -.169  | -.074  | .107   | .206   | .231   |
|           | CR9  | .002  | .252 | -.118  | -.178  | -.108  | .074   | .181   | .216   |

Referring now to FIG. 5, basic circuit theory may be used to calculate the resistor values shown in Table 1. For each desired output voltage equation represented by matrix V where the coefficients have been determined so as to give the desired output, there is a corresponding output voltage equation where the output to line L3 may be expressed generally as a function of the eight input voltages from line L1 or L2, the value of $R_5$ (5 kilohms), and the unknown values of $R_{LA}$, $R_{LL}$, $R_{V1}$, $R_{V2}$, $R_{V3}$, $R_{V4}$, $R_{V5}$ and $R_{V6}$.

The embodiment of the invention which has been described is an analog implementation. However, as will be understood by those skilled in the art, other analog implementations departing from the specific circuitry which has been described are possible. Further, and again as will be understood by those skilled in the art, the signal processing implemented with analog circuitry may also be implemented with software. In addition, it will be apparent to those skilled in the art that the present invention may be readily implemented in a data communication system where a patient is monitored at one site and signal processing takes place at a remote site.

In accordance with the method of the present invention, chest electrodes are attached at chest positions V1, V2, V3, V4, V5 and V6 of body 100 and limb electrodes are attached at positions RA, LA, and LL of body 100. Voltage signals produced by the electrodes in response to heart activity of body 100 are sensed and, from the sensed signals, a voltage signal substantially corresponding to the voltage that would be produced by a further chest electrode is synthesized. Using apparatus as described with reference to FIGS. 4 and 5, including the attachment of a ground electrode at position RL of body 100, voltage signals are sensed with reference to RL, and six voltage signals are synthesized-each synthesized signal corresponding to the signal that would be produced by a further chest electrode at one of chest positions V3R, V4R, V5R, V7, V8 and V9 of body 100 as shown in FIG. 3. The necessity to actually attach electrodes at positions V3R, V4R, V5R, V7, V8 and V9 in order to sense the corresponding voltage signals is avoided.

A variety of modifications, changes and variations to the invention are possible within the spirit and scope of the following claims. The invention should not be considered as restricted to the specific embodiment which has been described and illustrated with reference to the drawings.

I claim:

1. Signal processing apparatus for use with an electrocardiograph monitoring activity of the human heart, said apparatus comprising:
   (a) input means for receiving input signals from electrodes attached to the body of a subject whose heart activity is being monitored, said electrodes comprising chest electrodes positioned at conventional positions V1, V2, V3, V4, V5 and V6 of said body and limb electrodes positioned at conventional positions RA, LA and LL of said body;
   (b) signal processing means operatively connected to said input means for synthesizing a signal from said input signals when said electrodes are so positioned, said synthesized signal substantially corresponding to an unsynthesized signal that would be produced by a further chest electrode, if such a further chest electrode was used on said body at a chest position other than said conventional positions; and,
   (c) signal output means for providing said synthesized signal as an output to said electrocardiograph.

2. Apparatus as defined in claim 1, wherein said synthesized signal is a signal substantially corresponding to a signal from the group consisting of chest lead signals V3R, V4R, V5R, V7, V8 and V9.

3. Apparatus as defined in claim 1, wherein said apparatus includes means for providing as an output to said electrocardiograph from said output means unsynthesized signals corresponding to said input signals from said conventionally positioned limb and chest electrodes, said apparatus further including signal selection means for selectively directing to said output means:
   (a) said signals corresponding to said input signals; or
   (b) said synthesized signal.

4. Apparatus as defined in claim 3, wherein said synthesized signal is a signal substantially corresponding to a signal from the group consisting of chest lead signals V3R, V4R, V5R, V7, V8 and V9.

5. Apparatus as defined in claim 3, wherein said signal selection means comprises a switch switchable between:
   (a) a first position at which said unsynthesized signals corresponding to said input signals are directed to said output means; and,
   (b) a second position at which said synthesized signal is directed to said output means.

6. Apparatus as defined in claim 5, wherein said synthesized signal is a signal substantially corresponding to a signal from the group consisting of chest lead signals V3R, V4R, V5R, V7, V8 and V9.

7. Apparatus as defined in claim 3, wherein said input means includes means for receiving an input signal from a ground electrode positioned at conventional position RL of said body, and wherein:
   (a) input signals from said electrodes at positions V1, V2, V3, V4, V5, V6, RA, LA and LL are referred to RL; and,
   (b) output signals are referred to RA.

8. Signal processing apparatus for use with an electrocardiograph monitoring activity of the human heart, said apparatus comprising:
   (a) input means for receiving input signals from electrodes attached to the body of a subject whose heart activity is being monitored, said electrodes comprising chest electrodes positioned at conventional positions V1, V2, V3, V4, V5 and V6 of said body and limb electrodes positioned at conventional positions RA, LA and LL of said body;
   (b) signal processing means operatively connected to said input means for synthesizing signals from said input signals when said electrodes are so positioned, said synthesized signals substantially corresponding to unsynthesized signals that would be produced by further chest electrodes, if such further electrodes were used on said body at chest positions other than said conventional positions; and,
   (c) signal output means for providing said synthesized signals as an output to said electrocardiograph.

9. Apparatus as defined in claim 8, wherein said synthesized signals are signals substantially corresponding to signals from the group consisting of chest lead signals V3R, V4R, V5R, V7, V8 and V9.

10. Apparatus as defined in claim 8, wherein said apparatus includes means for providing as an output to said electrocardiograph from said output means unsynthesized signals corresponding to said input signals from said conventionally positioned limb and chest electrodes, said apparatus further including signal selection means for selectively directing to said output means:
    (a) said signals corresponding to said input signals; or,
    (b) said synthesized signals.

11. Apparatus as defined in claim 10, wherein said synthesized signals are signals substantially corresponding to signals from the group consisting of chest lead signals V3R, V4R, V5R, V7, V8 and V9.

12. Apparatus as defined in claim 10, wherein said signal selection means comprises a switch switchable between:
    (a) a first position at which said signals corresponding to said input signals are directed to said output means; and,
    (b) a second position at which said synthesized signals are directed to said output means.

13. Apparatus as defined in claim 12, wherein said synthesized signals are signals substantially corresponding to signals from the group consisting of chest lead signals V3R, V4R, V5R, V7, V8 and V9.

14. Apparatus as defined in claim 10, wherein said input means includes means for receiving an input signal from a ground electrode positioned at conventional position RL of said body, and wherein:
    (a) input signals from said electrodes at positions V1, V2, V3, V4, V5, V6, RA, LA and LL are referred to RL; and, (b) output signals are referred to RA.

15. A method of monitoring heart activity of a human body comprising the steps of:
   a) attaching chest electrodes at chest positions V1, V2, V3, V4, V5 and V6 of said body and attaching limb electrodes at positions RA, RL and LL of said body.
   b) sensing voltage signals produced by said electrodes in response to said heart activity; and,
   c) synthesizing from said sensed signals a voltage signal substantially corresponding to a voltage signal that would be produced by a further chest electrode, if such a further chest electrode was used on said body at a chest position other than said chest positions.

16. A method as defined in claim 15, wherein said synthesized signal is a signal substantially corresponding to a signal that would be produced by a further chest electrode located on said body at a position selected from the group consisting of chest positions V3R, V4R, V5R, V7, V8 and V9.

17. A method as defined in claim 15, including the step of attaching a ground electrode at position RL of said body and sensing said voltage signals from said position V1, V2, V3, V4, V5, V6, RA, LA and LL with respect to said ground electrode.

* * * * *